United States Patent [19]

Eden

[11] 4,446,249
[45] May 1, 1984

[54] COPPER CATALYST COMPOSITIONS FOR FLUID-BED OXYHYDROCHLORINATION OF ETHYLENE

[75] Inventor: Jamal S. Eden, Akron, Ohio

[73] Assignee: The B. F. Goodrich Company, Akron, Ohio

[21] Appl. No.: 378,928

[22] Filed: May 17, 1982

Related U.S. Application Data

[63] Continuation-in-part of Ser. No. 274,995, Jun. 18, 1981, abandoned, which is a continuation of Ser. No. 91,288, Nov. 5, 1979, abandoned.

[51] Int. Cl.³ .................... B01J 27/10; C07C 17/156
[52] U.S. Cl. .................................... 502/225; 570/243
[58] Field of Search ............... 570/243; 252/441, 442; 502/225

[56] References Cited

U.S. PATENT DOCUMENTS

| | | | |
|---|---|---|---|
| 2,271,056 | 1/1942 | Balcar et al. | 423/502 |
| 3,427,359 | 2/1969 | Rectenwald et al. | 570/243 |
| 3,488,398 | 1/1970 | Harpring et al. | 570/243 |
| 4,069,170 | 1/1978 | Blake | 252/441 |
| 4,124,534 | 11/1978 | Leitert et al. | 570/243 |

FOREIGN PATENT DOCUMENTS

| | | | |
|---|---|---|---|
| 659895 | 10/1964 | Canada | 570/243 |
| 701913 | 1/1965 | Canada | 570/243 |

*Primary Examiner*—P. E. Konopka
*Attorney, Agent, or Firm*—Carl W. Battle

[57] ABSTRACT

A fluidizable catalyst composition is provided having cupric chloride deposited on a fluidizable, modified gamma alumina support in which the support has incorporated, prior to the deposit of copper, from 0.5% to 3.0% by weight based on the weight of the support of at least one metal selected from the group consisting of potassium, lithium, rubidium, cesium, alkaline earth metals, rare earth metals, or combinations thereof. Such catalyst compositions are extremely useful as the fluid bed catalyst in the vapor phase oxyhydrochlorination reaction of ethylene, oxygen and hydrogen chloride to produce 1,2-dichloroethane. The use of the catalysts results in improved EDC efficiency based on ethylene and avoids operating problems caused by stickiness of the catalyst in the fluid bed. Incorporation of a combination of potassium and barium in the fluidizable gamma alumina support, prior to deposit of the copper, produces an excellent catalyst for a fluid bed ethylene oxyhydrochlorination process in which the vent gases from the process are recycled.

12 Claims, No Drawings

COPPER CATALYST COMPOSITIONS FOR FLUID-BED OXYHYDROCHLORINATION OF ETHYLENE

CROSS REFERENCE TO RELATED APPLICATIONS

This application is a continuation-in-part of application Ser. No. 274,995 filed on June 18, 1981, now abandoned which is a continuation of application Ser. No. 091,288 filed on Nov. 5, 1979 now abandoned.

BACKGROUND OF THE INVENTION

This invention pertains to fluid bed catalytic oxyhydrochlorination of ethylene to produce 1,2 dichloroethane, commonly called ethylene dichloride (EDC), and relates specifically to improved copper catalysts and their use in an ethylene oxyhydrochlorination reaction.

The production of chlorinated hydrocarbons by oxyhydrochlorination is known to the art. A known process for oxyhydrochlorination of ethylene to produce EDC, practiced in many commercial installations throughout the world, involves the reaction in the vapor phase over a fluidized catalyst bed, of a mixture of ethylene, hydrogen chloride (HCl) and oxygen or an oxygen containing gas (e.g., air), in the manner and under the conditions generally described in U.S. Pat. No. 3,488,398 granted to Harpring et al. In this process the molar ratio of ethylene to oxygen to HCl is in the range of about 1.0 to 1.2 moles of ethylene to about 0.55 to 0.9 moles of oxygen for each 2 moles of HCl, the temperature is in the range of 200° to 250° C., and the pressure is in the range of 10 to 50 psi.

The typical fluidized catalyst heretofore used in oxyhydrochlorination reactions consists of about 2% to 12% by weight of a copper compound, preferably copper chloride, as the active catalytic ingredient, uniformly deposited on fine particles of a fluidizable support. The support could be silica, kieselguhr, clay, fuller's earth, or preferredly alumina. The alumina support material can be gamma alumina, alpha alumina, the so-called microgel aluminas or other forms of "activated" alumina, of such a nature and particle size to be readily fluidizable without excessive catalyst loss from the reaction zone, and having the proper bulk density, resistance to attrition and particle size distributions. In the oxyhydrochlorination of ethylene, the alumina support typically used is gamma alumina having a surface area in excess of 50 $m^2/g$.

The standard ethylene oxyhydrochlorination catalyst, as above described, can desirably be improved in two significant respects.

First, it is desirable for the catalyst to effect a higher EDC efficiency based on ethylene (i.e., for the ethylene reactant to be more completely converted to EDC with less being converted to carbon oxides such carbon monoxide and carbon dioxide). In a high volume business such as the manufacture of EDC, small efficiency increases are very valuable. For example, in a one billion pound per year EDC plant, an EDC efficiency increase of only 1% results in a savings of about one million dollars annually. Increased EDC efficiency is particularly desirable if the ethylene oxyhydrochlorination process, as described in the Harpring et al patent (which in its exemplified embodiments used air to supply oxygen), is adapted to recycle the gases which would normally be vented to the atmosphere, in order to avoid releasing hydrocarbons and chlorinated hydrocarbons to the environment. This vent gas recycle variation of the ethylene oxyhydrochlorination process is described in more detail in U.S. Pat. Nos. 4,071,572 and 4,310,713.

Secondly, the typical copper on alumina fluidized catalyst exhibits a strong tendency to develop "stickiness" during the reaction, particularly at temperatures in excess of 225° C., which can cause severe disruption of process operations. This problem and a device and means for its partial control are described in U.S. Pat. No. 4,226,798 issued to Cowfer et al, and a method of controlling stickiness in such catalysts is described in copending application Ser. No. 239,806 filed on Mar. 2, 1981 in the name of Cowfer et al. Although these devices and methods are helpful, it is more practical and efficient to make catalysts which do not develop stickiness in the first place.

Finally, by way of background, it has been proposed in prior art patents to conduct oxyhydrochlorination reactions in a fluid bed in which the fluidized catalyst contains not only copper chloride but other metal chlorides like potassium chloride on the support. For example, U.S. Pat. No. 3,427,359 describes a catalyst composition for fluid-bed oxychlorination of hydrocarbons and partially chlorinated hydrocarbons consisting of copper chloride, an alkali metal chloride and a rare earth metal chloride supported on an inert carrier material, such as alpha alumina, having a surface area no greater than 10 $m^2/g$. Likewise, U.S. Pat. Nos. 4,069,170 and 4,124,534 and Canadian Pat. Nos. 695,895 and 701,913 teach the use of certain metal chlorides deposited with copper chloride on low surface area supports. However, when such metal chlorides are deposited on a high surface area support such as gamma alumina, and are used in a fluid bed ethylene oxyhydrochlorination process such as described above, the EDC efficiency does not improve and increased stickiness of the catalyst particles in the fluid bed occurs. Consequently the above prior art does not teach or suggest how to obtain the improvements stated above.

SUMMARY OF THE INVENTION

It has now been unexpectedly discovered that the incorporation of certain specified metals into a gamma alumina support prior to and independently of depositing copper on the support, results in an improved gamma alumina copper catalyst which, when used as the fluid bed catalyst in the oxyhydrochlorination of ethylene to EDC, results in significantly improved EDC efficiency based on ethylene and improved fluidization properties.

The metal so incorporated may be potassium, lithium, rubidium, cesium, an alkaline earth metal, a rare earth metal, or a mixture of one or more such metals. Incorporation of the specified metal or metals onto the gamma alumina support is accomplished by impregnating the support with an aqueous solution of a water soluble salt of the metal or metals in question, drying the wetted support, and then calcining the combination of the metal salt(s) and gamma alumina support at a temperature of 350° C. up to 600° C. for about 4 to 16 hours to produce a fluidizable, metal-modified gamma alumina having essentially the same physical characteristics as the gamma alumina support before the metal is incorporated therein. The calcining step at 350° C. to 600° C. prior to depositing the copper on the support, is an essential feature of this invention. The time of calcining should be sufficient to decompose the metal salt(s)

to the metal oxide(s). The total amount of added metal(s) in the gamma alumina support is in the range of 0.5% to about 3.0% by weight based upon the weight of the support.

After incorporation of the metal(s), copper, preferably as cupric chloride, is deposited on the metal-modified gamma alumina support in any known manner.

When the novel catalyst compositions are used in the fluid bed oxyhydrochlorination of ethylene to EDC under typical commercial reaction conditions (i.e., 225° C. and a 20 second contact time), the conversion of ethylene to EDC is usually above 98% (only about 2% of the ethylene converted goes to carbon oxide formation) so that the EDC efficiency based on ethylene (i.e., % conversion of ethylene times % yield EDC based on ethylene) is of the order of 96% or higher. This efficiency compares with a normal EDC efficiency in the order of 93 to 94% obtained using conventional, known copper on alumina catalyst compositions. Further, the catalyst compositions of this invention are significantly less "sticky" when used in the oxyhydrochlorination reaction. Accordingly, this invention provides, in addition to an improved catalyst composition, an improved fluid-bed ethylene oxyhydrochlorination process.

DETAILED DESCRIPTION OF THE INVENTION

The gamma alumina support material used in preparing the modified gamma alumina support, on which copper is later deposited to form the catalyst compositions of this invention, is readily available. The gamma alumina support material used has a surface area in the range of 60 to 200 $m^2/g$, a bulk density in the range of 0.9 to 1.1 grams per c.c., a pore volume in the range of 0.2 to 0.5 c.c. per gram and a particle size distribution such that about 75 to 92 weight percent of the particles are below 80 microns in diameter, about 40 to 50 percent are below 45 microns in diameter, and about 15 to 30 percent are below 30 microns in diameter, with no more than 1% to 5% of the particles larger than 200 microns or more and no more than 3% to 10% of the particles smaller than 20 microns. Such gamma alumina materials are relatively stable, mechanically strong and resistant to attrition so that excessive quantities are not lost from the fluid bed reaction zone when used as a catalyst support in fluid bed reactions.

It is recognized that some conventional gamma alumina support materials may inherently contain in addition to $Al_2O_3$ traces of metal oxides such as sodium oxide. It is understood that the use of such gamma alumina supports, without modification through prior incorporation of added amounts of the metals herein specified, forms no part of this invention.

The metal-modified gamma alumina support used in this invention is prepared by first wetting an unmodified gamma alumina support material, as above described, with an aqueous solution of a salt(s) of the required metal or metals. The wetted alumina is then dried at about 80° C. to 110° C. to remove water and then calcined for 4 to 16 hours at a temperature in the range of 350° C. to 600° C., during which time the added metal salt is converted to a metal oxide. An amount of the metal salt is chosen so that the final modified gamma alumina support contains from 0.5% to 3.0% by weight of the incorporated metal based on the weight of the support. The metal used in the aqueous solution can be in the form of any desired water soluble salt, such as a chloride or carbonate of (i) potassium, lithium, rubidium or cesium, preferably potassium or lithium; or (ii) of an alkaline earth metal such as calcium, strontium or barium, preferably barium; or (iii) of a rare earth metal, such as lanthanum or cerium, or a mixture of rare earth metals such as the mixture didymium which contains lanthanum and neodymium together with smaller amounts of praesodymium and samarium and even smaller amounts of other rare earth metals; or (iv) a mixture of salts of the metals recited, whether or not of the same class. The specific mixtures of potassium with barium, cesium, or lanthanum, or the mixture of barium with lanthanum are particularly desirable.

The modified gamma alumina support having 0.5% to 3.0% of metal incorporated therein, prepared as above described, possesses physical characteristics similar to that of the unmodified gamma alumina support. The copper salt such as cupric chloride can be deposited on the modified gamma alumina support using the same known techniques as used in formation of standard alumina-supported copper catalysts. The amount of copper deposited will depend on the activity desired and the specific fluidization characteristics of the support, and can be as little as 2% by weight or as much as 12% by weight based on the weight of the modified gamma alumina support material. The final catalyst composition containing the copper catalyst on the modified support is fluidizable like the support, but certain specific characteristics such as surface area and pore volume, for example, are, of course, modified by reason of the deposit of copper.

The catalyst compositions of this invention have a surface area in the range of 50 to 160 $M^2/g$, which is about 10% to 30% lower than that of the modified gamma alumina support before the deposit of copper. The preferred range of surface area is 100 to 150 $m^2/g$, and the most preferred range is 110 to 130 $m^2/g$.

The specific Examples set forth below illustrate the unique and unexpected characteristics of the catalyst compositions of this invention, and particularly point out the criticality of (a) using a high surface area gamma alumina support and (b) the addition of the metals prior to deposition of the copper on the modified gamma alumina support, to obtain improved catalyst compositions for the oxyhydrochlorination of ethylene to produce EDC. In the Examples, the fluid bed ethylene oxyhydrochlorination reaction to form EDC is conducted in a bench scale fluid bed reactor of 20 mm. to 30 mm. internal diameter and 24 inches height charged with 125 ml. to 300 ml. of the fluid bed catalyst composition as described. The amount of catalyst charged to the reactor determines the contact time between reactants and catalyst. The reactor is equipped with means for delivering the gaseous ethylene, oxygen (as air) and HCl through the fluid bed reactor zone, means for controlling the quantities of reactants and reaction conditions, and means for ascertaining from the effluent gases the conversion and yield of ethylene to EDC and carbon oxides.

Two types of Examples are presented. In the Comparative Examples, the data shows that (i) use of low surface area alumina supports as taught in the prior art and (ii) adding the metals concurrently with the deposition of the copper as taught in the prior art, does not increase the EDC efficiency of ethylene oxyhydrochlorination reactions, and often results in increased stickiness of the catalyst. In the Examples of the invention, the data shows that higher EDC efficiencies are obtained when using the improved catalysts and catalyst stickiness is reduced during operations. Further, the Examples show the scope of the various metals which are used to modify the gamma alumina support.

COMPARATIVE EXAMPLES

A series of experiments were performed to show the differences between prior art catalysts and catalysts of the invention. In the comparisons, the reactants ethylene, oxygen and hydrogen chloride, all in the gas phase, were feed to the reactor in a molar ratio of 1.0 mole of ethylene and 0.8 moles of oxygen for each 2.0 moles of hydrogen chloride, and were reacted at a temperature in the range of 220° C.–250° C. by passing the reactants through a fluidized catalyst bed to form EDC. The catalysts consisted of fluidizable alumina supports each containing about 10% by weight of cupric chloride. In the experiments, the fluidizable alumina support was either a gamma alumina having a surface area of 60 to 200 square meters per gram ($m^2/g$) or a support having a low surface area of about 30 $m^2/g$ or less, such as alpha alumina. The cupric chloride was deposited on the various fluidizable alumina supports by thoroughly mixing the alumina support with aqueous cupric chloride solution followed by drying the wetted mass to fluidity by heating on a steam bath and/or in an oven at temperatures up to about 275° C. for 4 to 8 hours. The cupric chloride fluidizable catalyst had a surface area lower than the starting fluidizable alumina by a factor of about 10 to 30 percent.

COMPARATIVE EXAMPLE A

In these experiments, the fluidizable alumina catalyst contained, in addition to the deposited cupric chloride, from 0.5% to 3.0% by weight of one or more other added metals. The added metals were Potassium and Barium. Incorporation of the added metal(s) in the cupric chloride-on-alumina-support catalyst was effected by four distinct procedures described as follows:

(1) Metal(s) added with the $CuCl_2$. In this preparation, the starting gamma alumina support was treated with an aqueous solution of salt(s) of the added metal(s) and an aqueous solution of cupric chloride, and the mixture dried to fluidity at a temperature of 275° C. concurrently with the cupric chloride. This procedure and conditions are those known to the art.

(2) Metal(s) added prior to the $CuCl_2$, with low temperature heating. In this preparation, the starting gamma alumina support was thoroughly mixed with an aqueous solution of salt(s) of the added metal(s), the wetted mass dried to fluidity, and the dry mass then heated at temperature of 275° C. The cupric chloride was then deposited in an independent second step using the same conditions and procedure for this step as described in (1) above.

(3) Metal(s) added prior to the $CuCl_2$, with calcining at 350° C. to 600° C. In this preparation, the procedure used was as the same as in (2) above except that the heating was at a temperature of 400° C. for 8 hours. This is the procedure of the present invention.

(4) Metal(s) added prior to the $CuCl_2$, with very high temperature calcination. In this preparation, the procedure was the same as (3) above except that the heating temperature was above 600° C.; i.e. 1060° C. for 24 hours. This demonstrably changed the nature of the alumina support by greatly decreasing its surface area. This is the procedure taught in Canadian Pat. Nos. 695,895 and 701,913.

The catalysts prepared were evaluated in an ethylene oxyhydrochlorination process to prepare EDC. Each catalyst was placed on the bottom of a laboratory fluid bed reactor 25 to 30 millimeters in diameter and 40 centimeters high; a stream of the reactant gases, $C_2H_4$, HCl and air (oxygen) at reaction temperature, was introduced at the bottom of the reactor to fluidize the catalyst and cause the reactant gases to pass through contacting the catalyst for a time of 15 to 20 seconds. The reacted gases passed out of the reactor in an effluent gaseous stream which was analyzed to determine percent conversion of reactants to EDC and yield of EDC and by-products, especially CO and $CO_2$. During the experiment being run (the duration of which was sufficient to assure as much stability in the fluid bed as possible, but was otherwise insignificant) the condition of the catalyst fluid bed in terms of stickiness of the particles was observed and rated using the Temperature Profile Test (TPT) as described in U.S. Pat. No. 4,266,798. Catalyst 1 had an overall TPT rating of 3.5; Catalyst 2 had an overall TPT rating of 3.25; and Catalyst 3, a catalyst composition of the invention, had an overall TPT rating of 1.0. The results of these experiments are shown in Table A.

TABLE A

Effect of the Procedure Used to Incorporate the Added Metal(s) On a Gamma Alumina Support Catalyst Constants
Starting Support: gamma alumina having a surface area of 142 $m^2/g^{(a)}$
Metal Salts: KCl, $BaCl_2$, $CuCl_2$
Weight Percent of Metals: 1% K, 1% Ba, 10% Cu

| Catalysts | Procedure Used | Surface Area after Treatment |
|---|---|---|
| 1 | (1), with $CuCl_2$ | 10 to 15% reduced |
| 2 | (2), prior to $CuCl_2$; heated to 275° C. for 8 hours | 15 to 20% reduced |
| 3 | (3), prior to $CuCl_2$; heated to 400° C. for 8 hours | 30% reduced |
| 4 | (4), prior to $CuCl_2$; heated to 1060° C. for 24 hours | 88% reduced (17 $m^2/g)^{(a)}$ |

Reactant Feed Ratio: $C_2H_4/O_2/HCl$ = 1.0/0.8/2.0

| Catalyst | Temperature (°C.) Initial | Temperature (°C.) Final | Contact Time (Seconds) | % $C_2H_4$ Conversion | % Yield Of EDC | % Yield Of CO | % Yield Of $CO_2$ | % EDC Efficiency | Stickiness Observed |
|---|---|---|---|---|---|---|---|---|---|
| 1 | 221 | 221 | 15 | 95.4 | 98.6 | 0.4 | 0.7 | 93.9 | no |
|   | 226 | 228 | 15 | 98.2 | 98.1 | 0.6 | 1.0 | 96.2 | yes |
|   | 220 | 223 | 17 | 97.6 | 98.4 | 0.5 | 0.8 | 95.9 | yes |

TABLE A-continued

Effect of the Procedure Used to Incorporate the Added Metal(s) On a Gamma Alumina Support Catalyst Constants
Starting Support: gamma alumina having a surface area of 142 m$^2$/g[a]
Metal Salts: KCl, BaCl$_2$, CuCl$_2$
Weight Percent of Metals: 1% K, 1% Ba, 10% Cu

|   |     |     |    |      |      |     |     |      |      |
|---|-----|-----|----|------|------|-----|-----|------|------|
|   | 225 | 233 | 17 | 99.0 | 97.8 | 0.7 | 1.1 | 96.8 | yes  |
|   | 219 | 245 | 20 | 97.9 | 98.4 | 0.5 | 0.8 | 96.2 | yes  |
|   | 225 | 250 | 20 | 99.7 | 97.3 | 0.8 | 1.4 | 97.0 | yes  |
| 2 | 221 | 222 | 15 | 96.7 | 97.9 | 0.6 | 1.2 | 94.6 | some |
|   | 226 | 230 | 15 | 98.2 | 97.0 | 0.9 | 1.7 | 95.2 | yes  |
|   | 221 | 221 | 17 | 97.6 | 98.1 | 0.6 | 1.0 | 95.6 | no   |
|   | 225 | 227 | 17 | 98.8 | 97.1 | 0.9 | 1.6 | 95.8 | yes  |
|   | 221 | 223 | 20 | 98.8 | 97.2 | 0.8 | 1.6 | 96.0 | yes  |
|   | 226 | 245 | 20 | 99.4 | 96.9 | 0.9 | 1.7 | 96.3 | yes  |
| 3 | 220 | 220 | 15 | 92.9 | 98.6 | 0.5 | 0.7 | 91.8 | no   |
|   | 226 | 226 | 15 | 96.6 | 98.0 | 0.7 | 1.0 | 94.5 | no   |
|   | 221 | 221 | 17 | 95.8 | 98.2 | 0.6 | 0.9 | 94.1 | no   |
|   | 225 | 225 | 17 | 97.4 | 97.7 | 0.7 | 1.2 | 95.1 | no   |
| 3 | 219 | 219 | 20 | 97.8 | 98.1 | 0.6 | 0.9 | 95.9 | no   |
|   | 226 | 226 | 20 | 99.1 | 97.2 | 0.9 | 1.4 | 96.3 | no   |
| 4 | 220 | 220 | 13 | 25.5 | 98.7 | 0.1 | 0.3 | 25.2 | no   |
|   | 225 | 225 | 13 | 31.9 | 98.7 | 0.1 | 0.3 | 30.5 | no   |
|   | 220 | 220 | 20 | 30.0 | 98.9 | 0.1 | 0.4 | 29.7 | no   |

[a] Measured using a High Speed Surface Area Analyzer made by Micromeritics Instrument Co., Model #2205.

Procedure (3) is the method of the present invention. Procedure (1) is the standard, known procedure for preparing ethylene oxyhydrochlorination catalysts. Although the data shows that the catalyst prepared using Procedure (1) yielded satisfactory EDC efficiency, the catalyst developed stickiness which would require very close operational control to avoid in a commercial process.

In comparing the data from the use of catalysts prepared using Procedures (2), (3), and (4), it is obvious that the degree of heat treatment employed to the gamma alumina support, after the metals are added but before the copper is deposited, has a significant effect on the overall effectualness of the catalyst. In procedure (2), although the EDC efficiency is satisfactory, the catalyst developed stickiness. In procedure (4), the catalyst's EDC efficiency was drastically reduced, well below any commercial utility. This was not suprising, as it is well known that high temperature calcination reduces the surface area of alumina and causes a change from a gamma to an alpha alumina structure having low surface area. It is apparent from the data that only Procedure (3), the method of this invention, produces a catalyst which combines high EDC efficiency without development of stickiness in the fluid bed.

COMPARATIVE EXAMPLE B

In another group of experiments, a rare earth metal was added in combination with potassium on an alpha-alumina support, a low surface area alumina as taught in U.S. Pat. Nos. 3,427,359; 4,069,170; and 4,124,534. The added metals were incorporated using Procedures (1) and (3) described in Comparative Example A above, while all other variables remained constant. The results of these experiments are shown in Table B. It is apparent from the data that the use of an alpha-alumina support of low surface area results in a very low EDC efficiency regardless of the procedure used. Hence, the data shows that the prevent invention is limited to high surface area gamma alumina supports.

TABLE B

Incorporating Added Metals on a Alumina Support
Catalyst Constants
Starting Support: alpha alumina having a surface are of 32 m$^2$/g
Metal Salts: KCl, LaCl$_2$, CuCl$_2$
Weight Percent of Metals: 1% K, 1% La, 10% Cu

| Catalysts | Procedure Used |
|---|---|
| 1 | (1), with CuCl$_2$ |
| 3 | (3), Prior to CuCl$_2$; heated to 400° C. for 8 hours. |

Reactant Feed Ratios: C$_2$H$_4$/O$_2$/HCl = 1.0/0.8/2.0

| Catalyst | Temperature (°C.) | Contact Time (Seconds) | % C$_2$H$_4$ Conversion | % Yield Of EDC | % EDC Efficiency |
|---|---|---|---|---|---|
| 1 | 225 | 20 | 25.8 | 98.9 | 34.2 |
| 3 | 225 | 20 | 30.0 | 98.9 | 29.6 |

COMPARATIVE EXAMPLE C

In still another group of experiments, Potassium was added to a gamma alumina support following Procedure (3), the method of this invention. This catalyst (Catalyst 1) was compared to a standard copper on gamma alumina catalyst, containing no added Potassium (Catalyst 2) which was prepared using Procedure (1), a known method to prepare oxyhydrochlorination catalysts. The results are given in Table C. It is apparent from the data that, at all operating conditions, the use of the Potassium-modified gamma alumina catalyst yields a significantly higher % EDC efficiency.

TABLE C

| Catalyst | Temperature (°C.) | Contact Time (Seconds) | % C$_2$H$_4$ Conversion | % Yield Of EDC | CO | CO$_2$ | % EDC Efficiency |
|---|---|---|---|---|---|---|---|
| 1 | 220 | 13 | 98.1 | 99.0 | 0.2 | 0.6 | 97.1 |
| 2 | 219 | 13 | 99.1 | 95.7 | 1.4 | 2.6 | 94.8 |
| 1 | 220 | 16 | 99.5 | 98.1 | 0.6 | 1.0 | 97.6 |
| 2 | 219 | 16 | 99.8 | 95.2 | 1.5 | 3.0 | 95.0 |
| 1 | 220 | 21 | 100  | 97.9 | 0.6 | 1.2 | 97.9 |
| 2 | 220 | 21 | 100  | 95.0 | 2.2 | 2.4 | 95.0 |
| 1 | 225 | 18 | 99.7 | 98.6 | 0.3 | 0.7 | 98.2 |
| 2 | 225 | 18 | 100  | 94.1 | 2.3 | 3.1 | 94.1 |
| 1 | 225 | 21 | 100  | 96.9 | 1.0 | 1.5 | 96.9 |

TABLE C-continued

| Catalyst | Temperature (°C.) | Contact Time (Seconds) | % C₂H₄ Conversion | % Yield Of EDC | % Yield Of CO | % Yield Of CO₂ | % EDC Efficiency |
|---|---|---|---|---|---|---|---|
| 2 | 225 | 21 | 100 | 94.1 | 2.4 | 2.9 | 94.1 |

EXAMPLE 1

This Example illustrates the preparation and use of catalyst compositions of the invention in ethylene oxyhydrochlorination reactions.

Four different catalyst compositions were prepared using the methods described as follows: (I) gamma alumina was impregnated with 1% aqueous $K_2CO_3$, dried in a steam bath and calcined for 8 to 10 hours at 400° C., after which the potassium-modified alumina support is impregnated with 10% cupric chloride, dried slowly, heated 8 to 10 hours at 275° C. and sieved to 80 to 325 mesh; (II) same as (I) except the metal modified gamma alumina support was calcined at 570° C.; (III) same as (I) except LiCl was used in place of $K_2CO_3$; and (IV) same as (I) except CsCl was used in place of $K_2CO_3$.

Each catalyst composition was then separately charged to the fluid bed reactor where ethylene, oxygen and HCl in the molar ratios of 1.0/0.8/2.0 were reacted to form EDC under the conditions and with the yields and efficiencies as shown in Table 1.

TABLE 1

| Catalyst | Reaction Temp. °C. | Reactants Contact Time Seconds | % Conv. C₂H₄ | % Yield CO | % Yield CO₂ | % Yield EDC | % Efficiency EDC |
|---|---|---|---|---|---|---|---|
| I | 220 | 13.1 | 98.1 | 0.21 | 0.58 | 99.0 | 97.1 |
|  | 226 | 12.9 | 99.1 | 0.60 | 0.95 | 98.1 | 97.2 |
|  | 220 | 14.4 | 98.6 | 0.62 | 0.82 | 98.4 | 97.0 |
|  | 225 | 14.2 | 99.5 | 0.54 | 0.95 | 98.2 | 97.8 |
|  | 221 | 16 | 99.5 | 0.59 | 1.03 | 98.1 | 97.6 |
|  | 225 | 17.5 | 99.7 | 0.27 | 0.70 | 98.6 | 98.2 |
|  | 220 | 21.1 | 100 | 0.59 | 1.21 | 97.9 | 97.9 |
| II | 221 | 10.4 | 97.4 | 0.27 | 0.42 | 99.1 | 96.7 |
|  | 221 | 11.5 | 98.2 | 0.33 | 0.69 | 98.8 | 97.0 |
|  | 225 | 11.4 | 98.2 | 0.26 | 0.54 | 98.9 | 97.1 |
|  | 230 | 11.3 | 98.7 | 0.17 | 0.33 | 99.2 | 97.9 |
|  | 235 | 11.2 | 100 | 0.59 | 0.83 | 98.0 | 98.0 |
| III | 220 | 11.0 | 98.6 | 0.15 | 1.19 | 98.3 | 97.0 |
|  | 225 | 10.9 | 99.7 | 0.32 | 1.33 | 97.9 | 97.5 |
|  | 220 | 13.2 | 99.5 | 0.18 | 1.37 | 98.1 | 97.6 |
|  | 225 | 13.1 | 100 | 0.73 | 1.55 | 97.2 | 97.2 |
|  | 220 | 15.8 | 99.7 | 0.71 | 1.42 | 97.4 | 97.2 |
| IV | 220 | 12.7 | 98.8 | 0.5 | 1.03 | 98.3 | 96.8 |
|  | 220 | 15.8 | 100 | 0.76 | 1.41 | 97.5 | 97.5 |
|  | 220 | 20.0 | 100 | 0.81 | 2.07 | 96.6 | 96.6 |

The data in Table 1 shows that the EDC efficiency with each catalyst composition and under each reaction condition, is of the order of 97 to 98%. Further, the fluid bed catalyst compositions did not develop "stickiness" in the use as often occurs when the alkali metal salt is deposited on the alumina support concurrently with the cupric chloride salt.

EXAMPLE 2

This Example illustrates further catalyst compositions of this invention and their use in fluid bed oxyhydrochlorination of ethylene to EDC. The catalyst composition is made by method (II) as stated in Example 1 except that 1% $Ba(OH)_2$ is used to prepare the modified gamma alumina support. This catalyst composition was used in the fluid bed oxyhydrochlorination of ethylene to EDC as described in Example 1 with a reaction temperature of 225° C., a reactant feed ratio of $C_2H_4/O_2/HCl = 1.0/0.8/2.1$, and a contact time of 10 seconds for a period of 14 to 18.5 hours. The % ethylene conversion, % EDC yield, and % EDC efficiency based on ethylene is shown in the following table:

| Elapsed Time Hours | % Conversion C₂H₄ | % EDC Yield | % EDC Efficiency |
|---|---|---|---|
| 14 | 98.9 | 97.7 | 96.6 |
| 15.5 | 99.0 | 98.2 | 97.2 |
| 17.5 | 99.0 | 98.3 | 97.3 |
| 18.5 | 99.1 | 97.5 | 96.6 |

EXAMPLE 3

This Example illustrates two more catalyst compositions of this invention which were prepared using rare earth metals, and their use in ethylene oxyhydrochlorination reactions. The catalyst compositions were prepared as in method (I) of Example 1, but using lanthanum chloride ($LaCl_3$) and chlorides of a mixture of rare earth metals (RE $Cl_3$) respectively. They were used as in Example 1 in the fluid bed oxyhydrochlorination of ethylene with the following results:

| Metal In Catalyst | Initial Temperature (°C.) | Contact Time (Seconds) | Reactant Feed Ratios (C₂H₄/O₂/HCl) | % C₂H₄ Conversion | % EDC Yield | % EDC Efficiency |
|---|---|---|---|---|---|---|
| La | 218 | 11 | 1.0/0.8/2.0 | 99.1 | 98.4 | 97.5 |
|  | 219 | 10 | 1.0/0.8/2.0 | 99.6 | 97.2 | 96.7 |
|  | 221 | 8 | 1.0/0.8/2.0 | 98.9 | 98.0 | 96.9 |
|  | 218 | 11 | 1.0/0.8/2.13 | 99.3 | 98.3 | 97.6 |
| RE | 217 | 17 | 1.0/0.8/2.02 | 99.8 | 97.2 | 97.0 |

EXAMPLE 4

Another catalyst composition was prepared using method (I) and evaluated as in Example 1 except that a mixture of 1% KCl and 1% $BaCl_2$ was used to prepare the modified gamma alumina support on which the $CuCl_2$ was deposited, the reactant feed ratio was varied during the run, and the reaction was continued for a total of 282 hours. The data obtained is shown in the following Table:

TABLE IV

| Reactant Feed Ratio (C₂H₄/O₂/HCl) | Reaction Temp (°C.) | Contact Time (Seconds) | Elapsed Time (Hours) | % C₂H₄ Conversion | % EDC Yield | % EDC Efficiency |
|---|---|---|---|---|---|---|
| 1.0/0.8/2.0 | 225 | 10.5 | 6 | 98.2 | 99.8 | 98.3 |
|  | 225 | 10.5 | 27 | 98.3 | 99.4 | 97.8 |
|  | 220 | 12.7 | 48 | 100 | 99.2 | 99.2 |
|  | 218 | 12.7 | 168 | 98.7 | 99.0 | 97.7 |
| 1.0/0.8/2.17 | 218 | 11.1 | 222 | 96.6 | 99.6 | 96.3 |
|  | 220 | 11.0 | 233 | 96.9 | 99.1 | 96.1 |
|  | 215 | 13.7 | 236 | 96.8 | 99.6 | 96.4 |
|  | 220 | 13.6 | 279 | 98.5 | 99.2 | 97.7 |
|  | 218 | 17.3 | 282 | 99.3 | 99.0 | 98.4 |

The data shows that the yield of EDC from ethylene converted was above 99% even when the ratio of HCl in the reactants was increased and that % EDC efficiency was at 97 to 98% over a period of several days. This demonstrates that the catalyst composition of this Example is a particularly excellent fluid bed catalyst for ethylene oxyhydrochlorination conducted with oxygen recycle since the relative proportion of carbon oxides in the vent gas to be recycled is substantially reduced and any excess HCl in the feed resulting from recycling the vent gases would not reduce the % EDC efficiency based on ethylene.

EXAMPLE 5

The following example shows the preparation and use of further catalysts of this invention, and shows that the activity of the different catalysts can vary. For example, the use of Barium with Lanthanum as the added metals produces a highly active catalyst which is most beneficially employed at lower reaction temperatures. The catalysts were prepared using method (I) of Example 1, except that a mixture of (a) KCl and BaCl₂ was used, (b) a mixture of KCl and LaCl₃ was used, or (c) a mixture of BaCl₂ and LaCl₂ was used to modify the gamma alumina support. When used in an ethylene oxyhydrochlorination reaction at an C₂H₄/O₂/HCl feed ratio of 1.0/0.8/2.0, the following data was obtained:

| Metal in Catalyst | Temperature (°C.) | Contact Time (Sec.) | % C₂H₄ Conv. | % Yield Co | % Yield Co₂ | % EDC Yield | % EDC Efficiency |
|---|---|---|---|---|---|---|---|
| KBa | 225 | 19 | 99.5 | .62 | .82 | 98.0 | 97.5 |
| KLa | 225 | 10.7 | 99.6 | .16 | 1.14 | 98.4 | 98.0 |
|  | 225 | 20 | 100 | .85 | 2.45 | 96.0 | 96.0 |
| BaLa | 215 | 12.5 | 100 | .74 | 2.02 | 97.0 | 97.0 |
|  | 215 | 15.5 | 100 | .25 | 2.27 | 97.1 | 97.1 |
|  | 220 | 20 | 100 | 1.64 | 5.13 | 92.5 | 92.5 |

EXAMPLE 6

Two catalysts of this invention were prepared following method (I) of Example 1 using a 1% KCl salt solution and a 1% or 2% CeCl₃ salt solution as the modifying metals. The catalysts were used in an ethylene oxyhydrochlorination reaction where the contact time between catalyst and reactants was varied. The reactant feed stream of ethylene/oxygen/hydrogen chloride was maintained at 1.0/0.8/2.0 throughout the runs. As expected, increased contact time increased the yield of carbon oxides and decreased the yield of EDC. However, EDC efficiency still remained high.

|  | % Conversion C₂H₄ | % Conversion HCl | % Yield CO + CO₂ | % Yield EDC | % EDC Efficiency |
|---|---|---|---|---|---|
| Metal in Catalyst: 1 K, 1 Ce |  |  |  |  |  |
| Temp. 215° C. |  |  |  |  |  |
| C.T. 18.9 sec. | 98.9 | 96.4 | 0.78 | 98.9 | 97.7 |
| 22.4 sec. | 99.7 | 97.0 | 1.2 | 98.3 | 98.0 |
| 28.1 sec. | 100 | 98.1 | 2.12 | 97.4 | 97.4 |
| 36.0 sec. | 99.9 | 96.8 | 2.23 | 97.3 | 97.1 |
| Temp. 220° C. |  |  |  |  |  |
| C.T. 18.9 sec. | 99.4 | 96.4 | 1.04 | 98.5 | 98.0 |
| 22.4 sec. | 99.6 | 97.3 | 1.39 | 98.2 | 97.8 |
| 28.1 sec. | 99.7 | 97.8 | 2.16 | 97.4 | 97.1 |
| Metal in Catalyst: 1 K, 2 Ce |  |  |  |  |  |
| Temp. 218° C. |  |  |  |  |  |
| C.T. 21.6 sec. | 99.8 | 96.4 | 1.28 | 98.2 | 98.0 |
| 25.5 sec. | 100 | 97.5 | 1.93 | 97.5 | 97.5 |
| 32.2 sec. | 100 | 97.9 | 2.87 | 96.5 | 96.5 |

EXAMPLE 7

In still another group of experiments, various metals were added to a gamma alumina support using method (I) of this invention as described above. As a comparison, a standard ethylene oxyhydrochlorination catalyst was prepared using Procedure (1) of Comparative Example A (except no added metal was incorporated) and was also evaluated. Reaction temperature was 225° C., contact time was 20 seconds, and the C₂H₄/O₂/HCl ratio was 1.0/0.8/2.0. The results show that the incorporation of the added metal(s), followed by heating at 350° C. to 600° C. prior to the deposition of the copper, significantly improves the EDC efficiency over that of a catalyst having no added metals and prevents the development of stickiness in the fluid bed.

Effect of Added Metal(s)

| Variables In Catalyst Preparation | | | | |
|---|---|---|---|---|
| Added Metal Salts | % Added Metal | % Cupric Chloride | % EDC Efficiency | Observed Stickiness |
| None | None | 10 | 91.2 | Often Sticky |
| None | None | 7.0 | 86.6 | Often Sticky |
| None | None | 3.5 | 91.5 | Often Sticky |
| KCl | 0.5 K | 10 | 96.5 | Non-Sticky |
| K$_2$CO$_3$ | 1.0 K | 10 | 97.4 | Non-Sticky |
| LiCl | 1.0 Li | 10 | 97.3 | Non-Sticky |
| CsCl | 1.0 Cs | 10 | 97.0 | Non-Sticky |
| Ba(OH)$_2$ | 1.0 Ba | 10 | 96.9 | Non-Sticky |
| LaCl$_3$ | 1.0 La | 10 | 97.2 | Non-Sticky |
| CeCl$_3$ | 1.0 Ce | 10 | 94.2 | Non-Sticky |
| KCl BaCl$_2$ | 0.50 K 0.60 Ba | 4.83 | 97.5 | Non-Sticky |
| KCl LaCl$_3$ | 1.0 K 1.0 La | 10 | 97.2 | Non-Sticky |
| BaCl$_2$ LaCl | 1.0 Ba 1.0 La | 10 | 96.7 | Non-Sticky |

I claim:

1. A catalyst composition consisting essentially of 2% to 12% by weight of copper, as cupric chloride, on a fluidizable gamma alumina support having a surface area of about 60 to about 200 m$^2$g, wherein said support is modified prior to the deposit of copper by incorporating in it from 0.5% to 3.0% by weight based on the weight of the support of at least one added metal selected from the group consisting of potassium, lithium, rubidium, cesium, alkaline earth metals, rare earth metals and combinations thereof, by admixing a water soluble salt of the metal(s) with the gamma alumina support, drying the mix, and calcining the mix at 350° C. to 600° C. for about 4 to about 16 hours and before the copper is deposited.

2. The catalyst composition of claim 1 wherein the metal incorporated in the gamma alumina support is potassium.

3. The catalyst composition of claim 1 wherein the metal incorporated in the gamma alumina support is cesium.

4. The catalyst composition of claim 1 wherein the metal incorporated in the gamma alumina support is lithium.

5. A catalyst composition of claim 1 wherein the metal incorporated in the gamma alumina support is an alkaline earth metal.

6. The catalyst composition of claim 5 wherein the metal incorporated in the gamma alumina support is barium.

7. A catalyst composition of claim 1 wherein the metal incorporated in the gamma alumina support is a rare earth metal.

8. The catalyst composition of claim 7 wherein the metal incorporated in the gamma alumina support is lanthanum.

9. The catalyst composition of claim 1 wherein the metals incorporated in the gamma alumina support are potassium and barium.

10. The catalyst composition of claim 1 wherein the metals incorporated in the gamma alumina support are potassium and lanthanum.

11. The catalyst composition of claim 1 wherein the metals incorporated in the gamma alumina support are potassium and cesium.

12. The catalyst composition of claim 1 wherein the metals incorporated in the gamma alumina support are barium and lanthanum.

* * * * *